United States Patent
Hirose

(10) Patent No.: US 9,658,175 B2
(45) Date of Patent: May 23, 2017

(54) X-RAY ANALYZER

(71) Applicant: HITACHI HIGH-TECH SCIENCE CORPORATION, Minato-ku, Tokyo (JP)

(72) Inventor: Ryusuke Hirose, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 265 days.

(21) Appl. No.: 14/662,906

(22) Filed: Mar. 19, 2015

(65) Prior Publication Data
US 2015/0268180 A1    Sep. 24, 2015

(30) Foreign Application Priority Data
Mar. 20, 2014  (JP) .................................. 2014-058390

(51) Int. Cl.
*G01N 23/223* (2006.01)

(52) U.S. Cl.
CPC ..... *G01N 23/223* (2013.01); *G01N 2223/076* (2013.01); *G01N 2223/323* (2013.01)

(58) Field of Classification Search
CPC ........... G01N 23/223; G01N 2223/076; G01N 2223/323
See application file for complete search history.

(56) References Cited

U.S. PATENT DOCUMENTS

| | | | |
|---|---|---|---|
| 2002/0057759 A1* | 5/2002 | Ferrandino | G01N 23/223 378/84 |
| 2009/0213996 A1* | 8/2009 | Matoba | G01N 23/223 378/204 |
| 2010/0046701 A1 | 2/2010 | Matoba | |
| 2011/0135190 A1* | 6/2011 | Maad | A61B 6/0407 382/154 |
| 2012/0051507 A1* | 3/2012 | Hasegawa | G01N 23/223 378/44 |

FOREIGN PATENT DOCUMENTS

| | | |
|---|---|---|
| JP | 5-118999 A | 5/1993 |
| JP | 2006-329944 A | 12/2006 |
| JP | 2011-47898 A | 3/2011 |
| JP | 4650330 B2 | 3/2011 |
| JP | 5269521 B2 | 8/2013 |

* cited by examiner

*Primary Examiner* — Glen Kao
(74) *Attorney, Agent, or Firm* — Brinks Gilson & Lione

(57) ABSTRACT

An X-ray analyzer is provided with: a sample stage on which a sample is disposed; an X-ray source configured to irradiate the sample with a primary X-ray at a first angle; a detector configured to detect a secondary X-ray generated from the sample; a position adjustment mechanism configured to adjust a relative position between the sample stage and the primary X-ray; a first light source configured to emit a first light beam at a second angle toward a focal position of the primary X-ray or toward a predetermined position; and a second light source configured to emit a second light beam at a third angle toward the focal position or toward the predetermined position, wherein the first light beam and the second light beam are configured to have visibility sufficient for enabling visual distinction.

8 Claims, 5 Drawing Sheets

X-RAY ANALYZER

RELATED APPLICATIONS

This application claims priority under 35 U.S.C. §119 to Japanese Patent Application No. 2014-058390 filed on Mar. 20, 2014, the entire contents of which is hereby incorporated by reference.

BACKGROUND

1. Technical Field

The present invention relates to an X-ray analyzer, which is capable of detecting harmful substances and the like to be used for screening a product and the like or for measuring the thickness of a target such as a plating film.

2. Description of the Related Art

An X-ray fluorescence analysis is used by irradiating X-rays emitted from an X-ray source to a sample, obtaining a spectrum from energy by an X-ray detection device detecting X-ray fluorescence which corresponds to a characteristic X-ray emitted from the sample, and performing qualitative analysis, quantitative analysis, or measurement of a film thickness. In this X-ray fluorescence analysis, the sample is not destroyed and is analyzed rapidly, and thus this X-ray fluorescence analysis is widely used in a process-quality control and the like. Recently, high accuracy and high sensitivity are promoted to allow a small amount to be measured and particularly, spread use is expected as an analysis method of detecting harmful substances included in a material, a compound electronic component, or the like.

In an apparatus of performing this X-ray fluorescence analysis, a sample being a measuring target is required to be aligned to an irradiation position (position in a horizontal direction) of a primary X-ray applied onto a sample and a focal position (position in a height direction). In the related art, as position adjustment in the horizontal direction, for example, JP-A-2007-292476 discloses a method of setting the irradiation position of the primary X-ray and a sample observation position (for example, the center of a sample observation image obtained by a CCD camera) to be matched with each other. JP-A-2006-329944 discloses a method of irradiating the irradiation position of the primary X-ray with a laser beam and thus confirming a measurement position by directly performing viewing or using a sample observation image.

JP-A-H05-118999 discloses a method in which a distance between the irradiation position of the primary X-ray and the sample observation position (for example, the center of the sample observation image) is stored or measured in advance, the sample is disposed at a measurement position in the observation image, and then the sample is moved by the distance stored or measured in advance to the irradiation position of the primary X-ray.

As position adjustment in height direction, for example, JPA-2006-329944 discloses a method of setting the focal position (height position) of the primary X-ray and a focus in the sample observation image to be matched with each other. In addition, JP-A-2006-329944 discloses a method of emitting a laser beam from an inclination of the sample and setting the height position and the focal position of the primary X-ray to be matched with each other, the height position at which the center of the sample observation image or a designated position is irradiated with a laser beam. In other words, a method of moving the sample to the focal position of the X-rays by adjusting the height of the sample such that a laser beam is applied at the center of the sample observation image or the designated position.

US 2010/046701 A1 discloses a method in which the distance between the focal position of the primary X-ray and the height position (a position at which a laser beam emitted from the inclination is applied onto the center of the sample observation image or a focal position of the sample observation image) is stored or measured in advance, the height position is designated in the sample observation image by using the above-described method, the sample is set to be the height position designated by using the sample observation image and then the sample is moved by the distance measured in advance, and thus the sample is moved to the focal position of the primary X-ray.

JP-A-2011-047898 discloses a method of a laser displacement meter or the like measuring the height of an application point of the primary X-ray.

The technologies in the related art may have the following problems.

That is, in the technologies of the related art, it is sometimes difficult for an operator to discriminate whether a height position of the sample is near or far compared to a focal position of the primary X-ray, with direct viewing when a sample is disposed on a sample stage. For this reason, it may be necessary that a sample observation image is viewed through a CCD camera or the like, in order to perform the discrimination and operability is degraded. In using a laser beam, when a height is shifted to the extent that a laser beam does not enter into the sample observation image, when a focus is largely shifted, or the like, rough adjustment of the height may be required. However, there may also be a case where it is difficult for the operator to discriminate whether the height position of the sample is near or far, when the rough adjustment of the height is performed.

SUMMARY

The present invention has been made in view of the above-described circumstances, and one of objects of the present invention is to provide an X-ray analyzer that enables easy discrimination of whether a height position of a sample is near or far to or from a focal position of a primary X-ray, with direct viewing and easily performs position adjustment.

According to an exemplary embodiment of the present invention, there is provided an X-ray analyzer including: a sample stage on which a sample is disposed; an X-ray source configured to irradiate the sample with a primary X-ray at a first angle; a detector configured to detect a secondary X-ray generated from the sample by being irradiated with the primary X-ray; a position adjustment mechanism configured to adjust a relative position between the sample stage and the primary X-ray; a first light source configured to emit a first light beam at a second angle toward a focal position of the primary X-ray or toward a predetermined position which is apart from the focal position at a predetermined distance and at the same height as the focal position in a horizontal direction; and a second light source configured to emit a second light beam at a third angle toward the focal position or toward the predetermined position, the third angle being different from the first angle and the second angle. The first light beam and the second light beam are configured to have visibility sufficient for enabling visual distinction between the first light beam and the second light beam on the sample stage or on the sample disposed on the sample stage when the first light beam and the second light beam are irradiated on the sample stage or on the sample disposed on the sample stage.

BRIEF DESCRIPTION OF THE DRAWINGS

The above and other aspects of the present invention will become more apparent and more readily appreciated from the following description of illustrative embodiments of the present invention taken in conjunction with the attached drawings, in which:

FIGS. 2A and 2B are explanation diagrams when directly viewed from a sample stage, wherein FIG. 2A shows a case where irradiation positions of a first light beam and a second light beam coincide with a focal position, and wherein FIG. 2B shows a case where the irradiation positions of the first light beam and the second light beam are mutually shifted in an orthogonal direction to a direction of moving the irradiation positions of the first light beam and the second light beam;

DETAILED DESCRIPTION OF THE PREFERRED EMBODIMENTS

Figure 1:
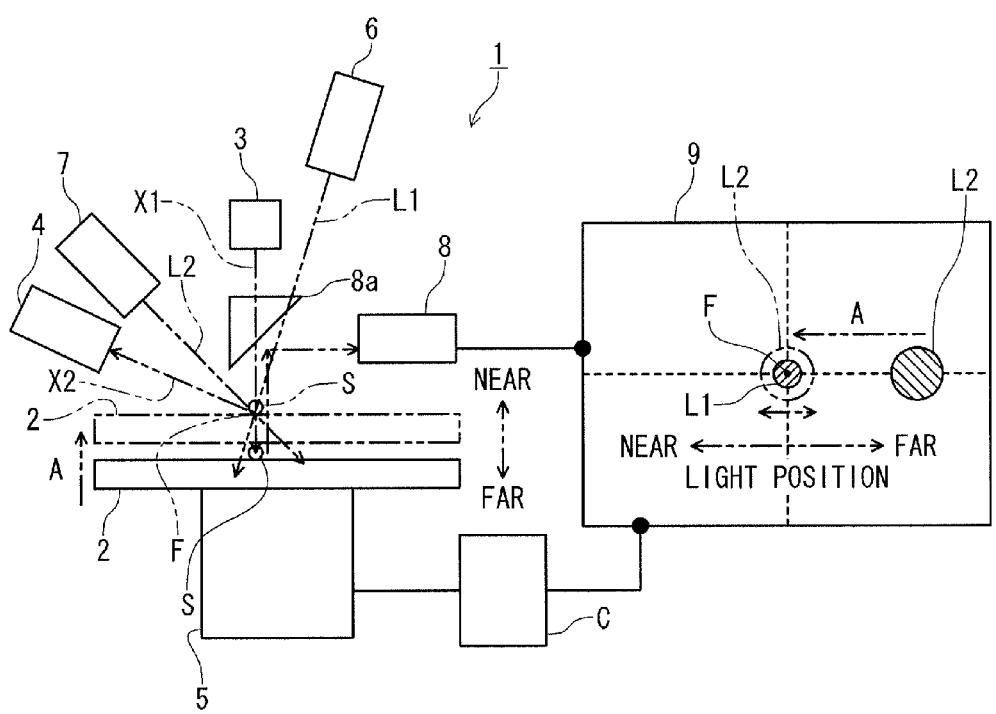
FIG. 1 is an overall configuration diagram schematically illustrating a first embodiment of an X-ray analyzer according to the present invention.

Hereinafter, a first embodiment of an X-ray analyzer according to the present invention will be described with reference to FIGS. 1 and 2.

An X-ray analyzer 1 according to this embodiment is an X-ray fluorescence analyzing apparatus that detects, for example, X-ray fluorescence as a secondary X-ray. As illustrated in FIG. 1, the X-ray analyzer 1 includes a sample stage 2 on which a sample S is allowed to be disposed, an X-ray source 3 that irradiates the sample with a primary X-ray X1, a detector 4 that detects a secondary X-ray X2 generated from the sample which is irradiated with the primary X-ray X1, a position adjustment mechanism 5 that adjusts a relative position between the sample stage 2 and the primary X-ray X1, a first light source 6 that irradiates a focal position F of the primary X-ray X1 with a first light beam L1, a second light source 7 that applies a second light beam L2 at an angle different from the first light beam L1 and the primary X-ray X1 toward the focal position F, an observation mechanism 8 that includes an optical system 8a enabling observation of the sample stage 2, and a controller C that controls the position adjustment mechanism 5.

The first light beam L1 and the second light beam L2 have visibility of enabling distinction between the sample stage 2 and the sample S which is disposed on the sample stage 2, by sight when the sample stage 2 or the sample S which is disposed on the sample stage 2 is irradiated with the first light beam L1 and the second light beam L2. In this embodiment, the first light beam L1 and the second light beam L2 have different colors from each other, and a diameter of a beam spot on the sample stage for the first light beam L1 is different from a diameter of a beam spot on the sample stage 2 for the second light beam L2.

The focal position F of the primary X-ray X1 is at a position at which a diameter of a beam spot for the primary X-ray X1 becomes the minimum.

The observation mechanism 8 is provided with a CCD camera that captures a sample observation image including the first light beam L1 and the second light beam L2 with which the sample S on the sample stage 2 and the sample stage 2 are irradiated and that obtains the sample observation image as image data.

The optical system 8a is provided with a half mirror or a beam splitter which is arranged on an optical axis of the primary X-ray X1. The optical system 8a causes the primary X-ray X1 as it is to pass through the optical system 8a toward the sample stage 2, and changes an optical axis of the observation mechanism 8 so as to be directed toward the sample stage 2 and enables capturing of the sample observation image.

The controller C has a function to adjust a relative position between the sample stage 2 and the primary X-ray X1 by causing the position adjustment mechanism 5 to move the sample stage 2 based on the image data, and to cause a position of the sample S, an irradiation position of the first light beam L1, and an irradiation position of the second light beam L2 to coincide with each other.

The controller C is provided with to a computer configured by a CPU and the like and includes a display unit 9 allowing the sample observation image and an analysis result to be displayed. The sample observation image is displayed on the display unit 9, as illustrated in FIG. 1 and the center of the sample observation image corresponds to an irradiation position of the primary X-ray X1.

The sample stage 2 may place the sample S, and the position adjustment mechanism 5 corresponds to an XY axial stage and a Z axial stage which arrange the sample stage 2 on an upper portion of the position adjustment mechanism 5 and are controlled by the controller C to allow the sample stage 2 to be advanced and retreated in an XY direction (horizontal direction) and a Z direction (vertical direction).

The X-ray source 3 is provided with an X-ray tube bulb that enables irradiation with the primary X-ray X1 and emits an X-ray as the primary X-ray X1 from a window formed from a beryllium foil and the like. A voltage which is applied between a filament (cathode) and a target (anode) causes thermoelectrons which are generated from the filament (cathode) in the tube bulb to accelerate and to collide with W (tungsten), Mo (molybdenum), Cr (chrome), and the like of the target, and thereby the X-ray is generated. A light collection element (not illustrated) is disposed on a tip end side of the X-ray source 3. The light collection element such as a monocapillary, a collimator, and a polycapillary, collects the primary X-ray X1 and irradiates the sample S on the sample stage 2 with the collected primary X-ray X1.

The detector 4 is provided with a semiconductor detection element (for example, a Si (silicon) element which is a diode having a pin structure) (not illustrated) which is disposed on an X-ray incident window. The detector 4 generates a current pulse corresponding to one X-ray photon if the one X-ray photon is incident. A momentary current value of the current pulse is proportional to energy of an incident characteristic X-ray. The detector 4 is set so as to convert the current pulse which is generated by the semiconductor detection element into a voltage pulse, to amplify the converted voltage pulse, and to output the amplified voltage pulse as a signal.

The X-ray analyzer 1 is provided with an analyzer (not illustrated) that is connected to the detector 4 and analyzes the signal from the detector 4. The analyzer may be a pulse height analyzer (multichannel pulse height analyzer) that obtains a pulse height of the voltage pulse from the signal to generate an energy spectrum.

The first light source 6 emits, for example, a green or blue first light beam L1 and the second light source 7 emits, for example, a red or white second light beam L2. The second light beam L2 is set to have a diameter of a beam spot in the sample stage 2 which is larger than a diameter of a beam spot for the first light beam L1. For example, the diameter of the beam spot for the first light beam L1 is 0.4 mm and the diameter of the beam spot for the second light beam L2 is set to 1.0 mm.

The sample stage 2 or the sample S disposed on the sample stage 2 is irradiated with the first light beam L1 at an angle close to the optical axis (that is, the vertical direction of the sample stage 2) of the primary X-ray X1. The sample stage 2 is irradiated with the second light beam L2 at an angle to the optical axis of the primary X-ray X1, which is larger than that of the first light beam L1. The first light source 6 and the second light source 7 are disposed on opposite sides to each other with the optical axis of the primary X-ray X1 interposed between first light source 6 and the second light source 7. That is, in FIG. 1, the first light source 6 is arranged on a right side of the optical axis of the primary X-ray X1 and the second light source 7 is arranged on a left side of the optical axis of the primary X-ray X1. Accordingly, if an irradiation angle of the first light beam L1 to the optical axis of the primary X-ray X1 has a positive value, an irradiation angle of the second light beam L2 has a negative value. For example, the irradiation angle of the first light beam L1 is set to 5 degrees and the irradiation angle of the second light beam L2 is set to −45 degrees. Preferably, the irradiation angle of the first light beam L1 is set to be close to vertical as much as possible.

Figure 2A:
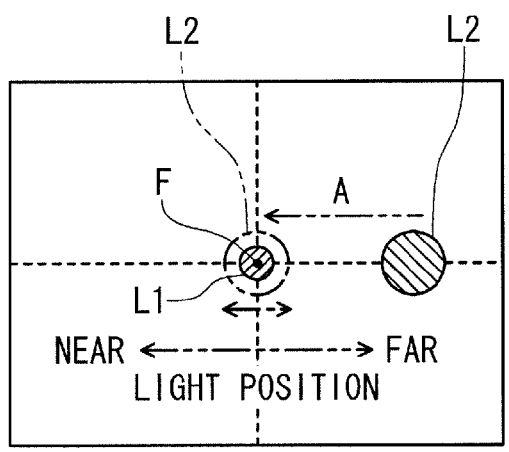

In the X-ray analyzer 1 according to this embodiment, in order to cause a position of the sample S on the sample stage 2 and the focal position of the primary X-ray X1 to coincide with each other, first both of the first light beam L1 and the second light beam L2 are applied onto the sample stage 2. At this time, it is possible to confirm with a direct viewing that a position at which the sample stage 2 is irradiated with the second light beam L2 is on a right side of a position of the first light beam L1, as illustrated in FIG. 2A, in a case where the sample stage 2 is farther than the focal position F of the primary X-ray X1. On the contrary, it is possible to confirm with a direct viewing that a position at which the sample stage 2 is irradiated with the second light beam L2 is on a left side of a position of the first light beam L1, in a case where the sample stage 2 is closer than the focal position F of the primary X-ray X1.

In this manner, it is possible to discriminate with a direct viewing whether a height position of the sample stage 2 is farther or closer than the focal position of the primary X-ray X1, based on a positional relationship of the first light beam L1 and the second light beam L2 which are applied to the sample stage 2 or the sample S disposed on the sample stage 2.

Then, the position adjustment mechanism 5 is controlled to adjust the height of the sample stage 2 in accordance with the height position of the sample stage 2 which is discriminated from the positional relationship of the first light beam L1 and the second light beam L2 such that positions of the first light beam L1 and the second light beam L2 which are applied to the sample stage 2 coincide with each other. For example, as illustrated in FIG. 2A, the sample stage 2 is moved in such a manner that the second light beam L2 on the sample stage 2 is moved in a direction of an arrow A to coincide with the first light beam L1.

The position adjustment mechanism 5 moves the sample stage 2 in the horizontal direction in a state where the first light beam L1 and the second light beam L2 coincide with each other on the sample stage 2 or the sample S disposed on the sample stage 2 and thus positions of the sample S on the sample stage 2, the first light beam L1, and the second light beam L2 are caused to coincide with each other. It is possible to cause a position of the sample S on the sample stage 2 to coincide with the focal position of the primary X-ray X1 through this operation.

In this embodiment, since the first light beam L1 is applied at an angle close to the vertical direction of the sample stage 2 which corresponds to an irradiation direction of the primary X-ray X1, a moving amount of the first light beam L1 which is applied to the sample stage 2 due to up and down movement of the sample stage 2 is smaller than that of the second light beam L2 on the sample stage 2. Since the second light beam L2 has an angle to the optical axis of the primary X-ray X1, which is larger than an angle of the first light beam L1, a moving amount of the second light beam L2 due to up and down movement of the sample stage 2 is greater than that of the first light beam L1 on the sample stage 2. Accordingly, a position of the sample S is matched with the first light beam L1 in a case where the horizontal direction is adjusted before the height position is adjusted, and thus it is possible to perform rough adjustment in such a manner that the sample S may be arranged to be near to the irradiation position of the primary X-ray X1. When the height position is adjusted, it is possible to easily adjust the height by mainly setting the second light beam L2 on the sample stage 2 or on the sample S disposed on the sample stage 2 as a reference. Accordingly, the first light beam L1 is mainly used for a horizontal position adjustment and the second light beam L2 is mainly used for a height position adjustment.

The position adjustment is performed by manually operating the position adjustment mechanism 5 with a direct viewing. However, the controller C automatically may control the position adjustment mechanism 5 to cause a position of the sample S, the irradiation position of the first light beam L1, and the irradiation position of the second light beam L2 to coincide with each other, based on the image data obtained by the observation mechanism 8. That is, the controller C automatically recognizes the first light beam L1 and the second light beam L2 from the image data captured by the observation mechanism 8, controls the position adjustment mechanism 5 so as to cause positions of the first light beam L1, the second light beam L2, and the sample S on the sample stage 2 to coincide with each other, and moves the sample stage 2.

In addition, rough adjustment referring to the above-described manual position adjustment may be performed prior to the position adjustment with viewing the sample observation image generated by the observation mechanism 8 or an automatic position adjustment performed by the controller C.

Figure 2B:
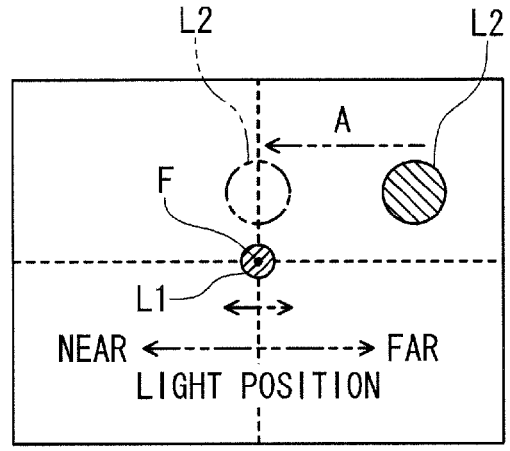

As illustrated in FIG. 2B, setting may be performed such that the irradiation positions of the first light beam L1 and the second light beam L2 are shifted in an orthogonal direction to a direction of moving the first light beam L1 and the second light beam L2 on the sample stage 2. For example, in FIG. 2B, only the second light beam L2 is separated from the focal position F at a predetermined distance in the orthogonal direction. In this case, a distance between the irradiation positions of the first light beam L1 and the second light beam L2 is obtained as a reference distance in a state where the height of the sample stage 2 is set to coincide with the height of the focal position F in advance.

When height adjustment is performed, the height of the sample stage 2 is adjusted until a distance between the first light beam L1 and the second light beam L2 becomes the reference distance, and thus it is possible to match the height of the sample stage 2 to the focal position F. That is, position adjustment is performed such that a predetermined disposition of the first light beam L1 and the second light beam L2 causes the distance between the first light beam L1 and the second light beam L2 to become the reference distance and thus it is possible to match the height to the focal position F.

Regarding adjustment of the horizontal direction, since the irradiation position of the first light beam L1 is the same as the focal position F in a state where the height positions coincide with each other, the sample stage 2 is moved in the horizontal direction such that the sample S is positioned at the position of the first light beam L1, and thus it is possible to match the sample S to the irradiation position of the primary X-ray X1.

In the X-ray analyzer 1 according to such this embodiment, when the sample stage 2 or the sample S disposed on the sample stage 2 is irradiated with the first light beam L1 and the second light beam L2 which are applied at different angles from each other, the first light beam L1 and the second light beam L2 have visibility of enabling recognition of the first light beam L1 and the second light beam L2 on the sample stage 2 or on the sample S disposed on the sample stage 2 by sight. Thus, it is possible to recognize the irradiation positions of the first light beam L1 and the second light beam L2 with a direct viewing and to discriminate whether the height of the sample S on the sample stage 2 is far or near, based on a relative relationship between the irradiation positions of the light beams.

A position at which the irradiation position of the first light beam L1 and the irradiation position of the second light beam L2 are interposed with each other is set as the focal position F, and thus it is possible to cause the sample S on the sample stage 2 and the focal position F of the primary X-ray X1 to coincide with each other by performing only coincidence of the irradiation position of the light beams with each other or adjustment of positions so as to have a predetermined disposition.

Since the first light beam L1 and the second light beam L2 have different colors from each other, it is possible to discriminate the first light beam L1 and the second light beam L2 with a direct viewing in accordance with the color of the applied ray.

Since the diameter of the beam spot on the sample stage 2 for the first light beam L1 is different from the diameter of the beam spot on the sample stage 2 for the second light beam L2, it is possible to discriminate the first light beam L1 and the second light beam L2 with a direct viewing in accordance with the size of the diameter of the beam spot.

The controller C controls the position adjustment mechanism 5 to cause a position of the sample S, the irradiation position of the first light beam L1, and the irradiation position of the second light beam L2 to coincide with each other, based on the image data of the sample observation image. Thus, it is possible to cause the focal position F of the primary X-ray X1 and the position of the sample S to coincide with each other through automatic adjustment based on the sample observation image and by sight.

Figure 3:
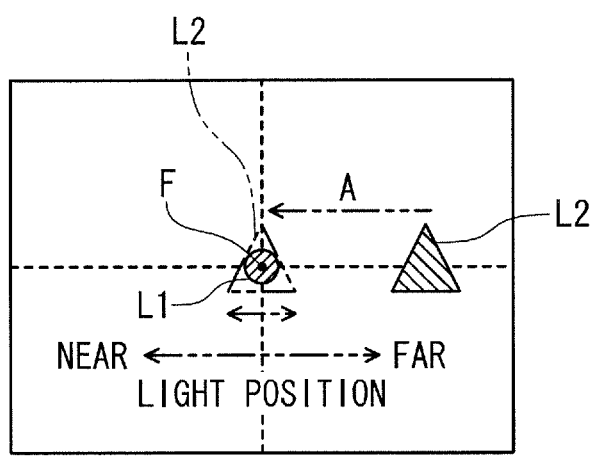
FIG. 3 is a view showing an example of a sample observation image for illustrating a second embodiment of the X-ray analyzer according to the present invention.
Figure 4:
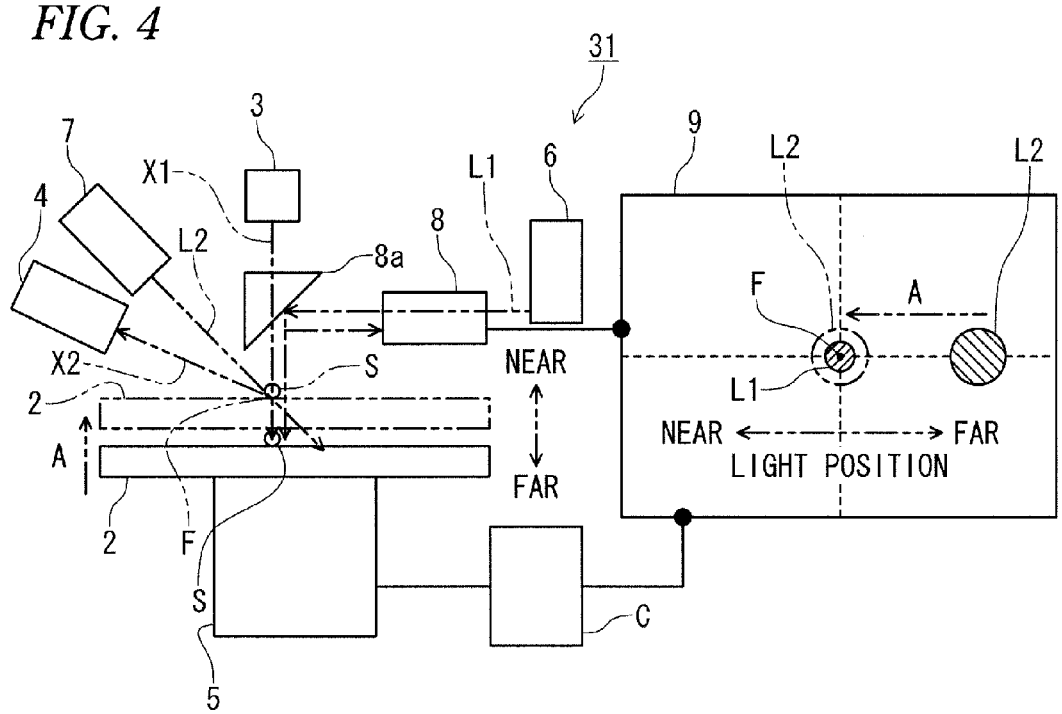
FIG. 4 is an overall configuration diagram schematically illustrating a third embodiment of the X-ray analyzer according to the present invention.

Next, second to fourth embodiments of the X-ray analyzer according to the present invention will be described below with reference to FIGS. 3 to 5. In the following descriptions for the embodiments, the same components as those described in the first embodiment are denoted by the same reference numerals and descriptions thereof will be omitted.

The second embodiment is different from the first embodiment in that, in the first embodiment, both irradiation shapes of the first light beam L1 and the second light beam L2 on the sample stage 2 are circular, but in the second embodiment, the irradiation shapes of the first light beam L1 and the second light beam L2 on the sample stage 2 are different from each other. That is, in the second embodiment, the irradiation shape of the first light beam L1 on the sample stage 2 is circular, but the irradiation shape of the second light beam L2 on the sample stage 2 is triangular.

In such the second embodiment, since the irradiation shapes of the first light beam L1 and the second light beam L2 on the sample stage 2 are different from each other, it is possible to discriminate the first light beam L1 and the second light beam L2 with a direct viewing in accordance with a difference between the irradiation shapes of the applied light beams.

The third embodiment is different from the first embodiment in that in the first embodiment, the first light beam L1 is slightly inclined to the irradiation direction (optical axis) of the primary X-ray X1 and applied, but in an X-ray analyzer 31 according to the third embodiment, the irradiation direction of the first light beam L1 is set to coincide with the optical axis of the primary X-ray X1. In addition, the third embodiment is different from the first embodiment in that in the first embodiment, the first light beam L1 emitted from the first light source 6 is directly applied toward the sample stage 2, but in the third embodiment, the first light beam L1 is applied toward the sample stage 2 in the same axis as the optical axis of the optical system 8a through the optical system 8a of the observation mechanism 8, as illustrated in FIG. 4.

In the third embodiment, the first light source 6 is disposed in such a manner that the first light beam L1 is emitted from a side of the optical system 8a to the optical system 8a in a state of coinciding with the optical axis of the observation mechanism 8. Accordingly, the first light beam L1 which is reflected toward the sample stage 2 by the optical system 8a corresponding to a half mirror or a beam splitter is applied toward the sample stage 2 in a state of coinciding with the irradiation direction (vertical direction of the sample stage 2) of the primary X-ray X1. In this disposition, the center of the sample observation image obtained by the observation mechanism 8 is irradiated with the first light beam L1 constantly. That is, the first light source 6 is a coaxial vertical illuminator of the observation mechanism 8. For easy viewing, FIG. 4 illustrates that the optical axis of the primary X-ray X1 is slightly shifted from the first light beam Ll. Similarly, FIG. 4 illustrates that the optical axis of the observation mechanism 8 is slightly shifted from the first light beam L1.

In the X-ray analyzer 31 according to such the third embodiment, since the irradiation direction of the first light beam L1 is set to coincide with the optical axis of the primary X-ray X1, if a position of the sample S is adjusted to be the irradiation position of the first light beam L1, it is possible to cause the sample S to be at the irradiation position of the primary X-ray X1 in the horizontal direction.

Figure 5:
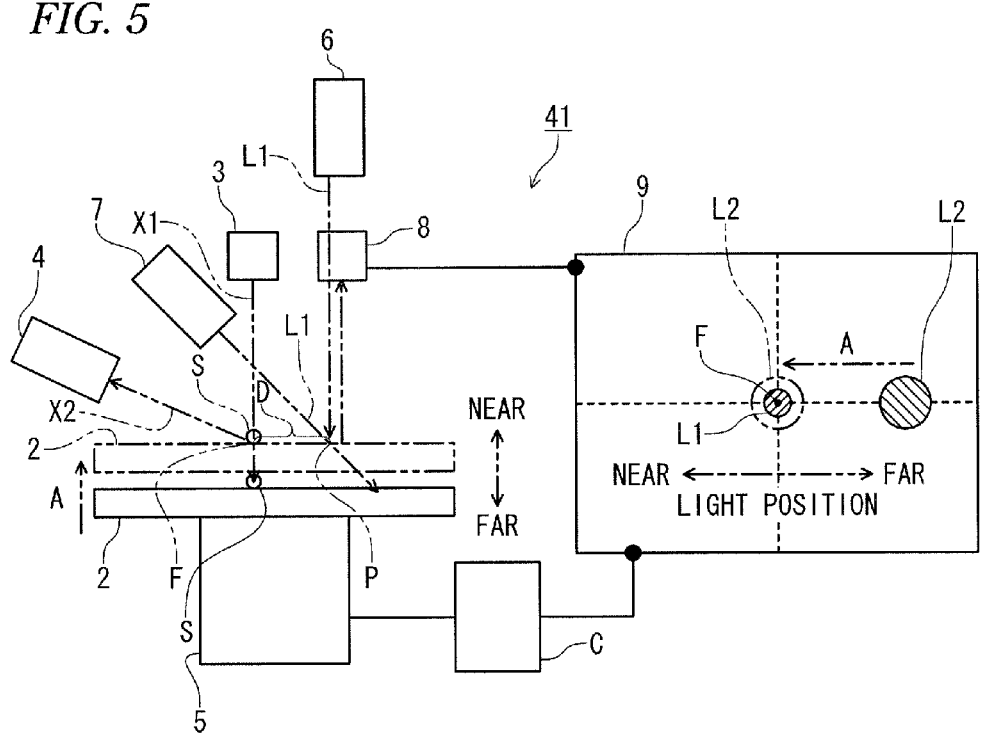
FIG. 5 is an overall configuration diagram schematically illustrating a fourth embodiment of the X-ray analyzer according to the present invention.

The fourth embodiment is different from the third embodiment in that in the third embodiment, the irradiation positions of the first light beam Ll and the second light beam L2 coincide with the focal position of the primary X-ray X1, but in an X-ray analyzer 41 according to the fourth embodiment, as illustrated in FIG. 5, the first light source 6 emits the first light beam L1 toward a predetermined position P which is separated from the focal position F of the primary X-ray X1 with a predetermined distance D at the same height as the focal position F in the horizontal direction, and the second light source 7 emits the second light beam L2 toward the predetermined position P at an angle different from the first light beam L1 and the primary X-ray X1.

In the fourth embodiment, the observation mechanism 8 is directly disposed at a position of enabling observation of the predetermined position P and the first light source 6 is directly disposed at a position of enabling irradiation of the predetermined position P with the first light beam L1 from the same direction as the observation mechanism 8, without using the optical system 8a.

Accordingly, the optical axis of the observation mechanism 8 coincides with the first light beam L1 and without using the optical system 8a, and setting is performed in such a manner that the center of the sample observation image is irradiated with the first light beam L1 constantly.

In the fourth embodiment, first, similarly to the first embodiment, the height position of the sample stage 2 is adjusted to be the height of the focal position of the primary X-ray X1, and then the sample stage 2 is moved in the horizontal direction and the irradiation positions of the first light beam L1 and the second light beam L2 on the sample stage 2 are caused to match with the center of the sample observation image. In this state, the irradiation positions of the first light beam L1 and the second light beam L2 coincide with the predetermined position P which is separated from the focal position F at the predetermined distance D.

Then, the position adjustment mechanism 5 moves the sample stage 2 by the predetermined distance D and thus it is possible to dispose the sample S at the focal position F of the primary X-ray X1 and to irradiate the sample S at the measurement position with the primary X-ray X1 and start analysis.

In the X-ray analyzer 41 according to such the fourth embodiment, since the first light beam L1 and the second light beam L2 are applied toward the predetermined position P which is separated from the focal position F of the primary X-ray X1 at the predetermined distance D in the horizontal direction, the center of the sample observation image is caused to match with the predetermined position P with which the irradiation positions of the first light beam L1 and the second light beam L2 coincide, and then the sample stage 2 is horizontally moved by the predetermined distance D. Thus, it is possible to cause the focal position F and the position of the sample S to match with each other.

The technical range of the present invention is not limited to the above-described embodiments and various changes may be applied in a range without departing from the purpose of the present invention.

For example, the above-described embodiments are applied to an energy analyzing type of an X-ray analyzer that measures the energy and strength of an X-ray using a pulse height analyzer. However, the above-described embodiments may be also applied to a wavelength dispersing type of an X-ray analyzer that causes a secondary X-ray to be spectral using a spectroscopic crystal and measures the wavelength and strength of an X-ray.

In the above-described embodiments, one point of a sample is analyzed, but when multiple points of the sample are analyzed and mapping is performed, the controller may drive the position adjustment mechanism to move the sample stage in the horizontal direction and to perform scanning through the automatic adjustment.

In the above-described embodiments, an example of the first light beam and the second light beam on the sample stage having different colors, different diameters of a beam spot, and different shapes from each other is described. However, as long as the first light beam and the second light beam have visibility of enabling distinction of those by sight, the first light beam and the second light beam may be other light beams having visibility. For example, when being applied onto the sample stage, the first light beam and the second light beam may be set in such a manner that luminance at bright spots of both light beams is clearly different. Although the first light beam and the second light beam have the same color, the same diameter of a beam spot, the same shape, and the same luminance, the first light beam and the second light beam may have visibility of enabling distinction by sight, by the first light source or the second light source causing either of the light beams to blink (i.e. repeatedly turned on and off). In this case, it is possible to easily discriminate the first light beam and the second light beam with a direct viewing in accordance with presence or absence of flickering.

What is claimed is:

1. An X-ray analyzer comprising:
a sample stage on which a sample is disposed;
an X-ray source configured to irradiate the sample with a primary X-ray at a first angle;
a detector configured to detect a secondary X-ray generated from the sample by being irradiated with the primary X-ray;
a position adjustment mechanism configured to adjust a relative position between the sample stage and the primary X-ray;
a first light source configured to emit a first light beam at a second angle toward a focal position of the primary X-ray or toward a predetermined position which is apart from the focal position at a predetermined distance and at the same height as the focal position in a horizontal direction; and
a second light source configured to emit a second light beam at a third angle toward the focal position or toward the predetermined position, the third angle being different from the first angle and the second angle,
wherein the first light beam and the second light beam are configured to have visibility sufficient for enabling visual distinction between the first light beam and the second light beam on the sample stage or on the sample disposed on the sample stage when the first light beam and the second light beam are irradiated on the sample stage or on the sample disposed on the sample stage.

2. The X-ray analyzer according to claim 1,
wherein the first light beam is configured to have a first color, and
wherein the second light beam is configured to have a second color that is different from the first color.

3. The X-ray analyzer according to claim 1,
wherein the first light beam is configured to have a first diameter of a beam spot on the sample stage, and
wherein the second light beam is configured to have a second diameter of a beam spot on the sample stage, the second diameter being different from the first diameter.

4. The X-ray analyzer according to claim 1,
wherein the first light beam is configured to have a first beam shape, and wherein the second light beam is configured to have a second beam shape that is different from the first beam shape.

5. The X-ray analyzer according to claim 1, wherein one of the first light beam and the second light beam is configured to blink.

6. The X-ray analyzer according to claim 1, wherein an irradiation direction of the first light beam is configured to be in parallel with an optical axis of the primary X-ray.

7. The X-ray analyzer according to claim 1 further comprising:
an observation mechanism comprising an optical system that is configured to enable observation of the sample stage,
wherein an irradiation direction of the first light beam is configured to coincide with an optical axis of the optical system to the sample stage.

8. The X-ray analyzer according to claim 1 further comprising:
an observation mechanism configured to obtain a sample observation image as image data, the sample observation image including an image of the first light beam and the second light beam irradiated on the sample stage or on the sample on the sample stage; and
a controller configured to control the position adjustment mechanism,
wherein the controller controls the position adjustment mechanism to cause a position of the sample, an irradiation position of the first light beam, and an irradiation position of the second light beam to coincide with each other, based on the image data.

* * * * *